United States Patent [19]

Cerff et al.

[11] Patent Number: 4,849,637
[45] Date of Patent: Jul. 18, 1989

[54] METHOD AND APPARATUS FOR CONTINUOUSLY MEASURING THE CONCENTRATION OF A GAS COMPONENT

[75] Inventors: Karlheinz Cerff, Kandel; Helmut Giraud, Stutensee-Spöck; Günther Krieg, Karlsruhe, all of Fed. Rep. of Germany

[73] Assignee: Kernforschungszentrum Karlsruhe GmbH, Karlsruhe, Fed. Rep. of Germany

[21] Appl. No.: 103,753

[22] Filed: Oct. 2, 1987

[30] Foreign Application Priority Data

Oct. 4, 1986 [DE] Fed. Rep. of Germany ....... 3633931

[51] Int. Cl.⁴ .......................................... G01J 3/42
[52] U.S. Cl. ................................. 250/345; 250/343; 250/344
[58] Field of Search ............... 250/339, 343, 344, 345; 372/20, 26

[56] References Cited

U.S. PATENT DOCUMENTS

| | | | |
|---|---|---|---|
| 3,805,074 | 4/1974 | McCormack | 250/343 |
| 3,932,040 | 1/1976 | Warncke | 250/430 |
| 4,142,160 | 2/1979 | Tsukada et al. | 372/46 |
| 4,410,273 | 10/1983 | Mantz et al. | 250/345 |
| 4,515,472 | 5/1985 | Welch | 250/342 |
| 4,684,805 | 8/1987 | Lee | 250/343 |

FOREIGN PATENT DOCUMENTS

| | | |
|---|---|---|
| 2362935 | 7/1974 | Fed. Rep. of Germany . |
| 3510052 | 8/1986 | Fed. Rep. of Germany . |
| 2165640 | 4/1986 | United Kingdom . |

OTHER PUBLICATIONS

Kemeny et al., "Utilization of Tunable Infrared Diode Lasers for the Determination of Labelled Molecules in Gas Mixtures", *Acta Physica Academiae Scientiarum Hungaricae,* vol. 48, No. 1, (1980), pp. 93–102.

Zasavitskii, et al., "Investigation of the Broadening of Absorption Lines of Molecular Gases by Methods of Pulsed Laser Diode Spectroscopy", *Soviet Journal of Quantum Electronics,* vol. 14, (No. 12), Dec. 1984, pp. 1615–1620.

Miles, et al., "Feedback-Induced Line Broadening in CW Channel-Substrate Planar Laser Diodes", APPLIED PHYSICS LETTERS, vol. 37, No. 11, Dec. 1st, 1980.

D. T. Cassidy et al., "Atmospheric Pressure Monitoring of Trace Gases Using Tunable Diode Lasers", APPLIED OPTICS, vol. 21, No. 7, Apr. 1982, pp. 1185–1620.

Hiroya Sano et al., "High Sensitivity Short-Path Monitoring of Trace Gases Employing PbSnTe Tunable Diode Laser", JAPANESE JOURNAL OF APPLIED PHYSICS, vol. 20, No. 11, Nov. 1981, pp. 2145–2153.

P. Pokrowsky et al., "Sensitive Detection of Hydrogen Chloride by Derivative Spectroscopy with a Diode Laser", OPTICAL ENGINEERING, vol. 23, No. 1, Jan./Feb. 1984, pp. 088–091.

*Primary Examiner*—Janice A. Howell
*Assistant Examiner*—William F. Rauchhol
*Attorney, Agent, or Firm*—Spencer & Frank

[57] ABSTRACT

A method and appparatus for continuously measuring the concentration of at least one component of a gas sample by means of a laser for the purpose of charging the gas sample with radiation at a frequency in the range of an absorption line of the component, and employing a detector device for receiving a measurement signal corresponding to the intensity of the transmitted radiation and an evaluation circuit. A single mode laser is employed which is linearly tuned about a gas specific absorption line by means of bandwidth modulation so that at least two different intensity measurement values are obtained for the transmitted radiation from which the extinction, and thus the concentration of the gas component, is determined.

11 Claims, 3 Drawing Sheets

METHOD AND APPARATUS FOR CONTINUOUSLY MEASURING THE CONCENTRATION OF A GAS COMPONENT

BACKGROUND OF THE INVENTION

The present invention relates to a method and apparatus of continuously measuring the concentration of at least one component in a gas sample. More particularly, the present invention relates to such a method and apparatus which employs a laser for charging the gas sample with radiation at a frequency in the range of an absorption line of the component, a detector device for receiving a measurement signal corresponding to the intensity of the transmitted radiation, as well as an evaluation circuit and devices for performing the measurements.

A method of the above type is disclosed in Federal Republic of Germany DE-OS No. 3,510,052. However, in the described process the absorption line must be tuned by way of a variation in temperature, and the absorption must be measured at a harmonic of the activated molecule.

The problem of continuously and selectively measuring specific trace gas concentrations, particularly of HF, exists particularly in industry. Solutions have been attempted wich provide for the use of wet chemical analysis methods. While such methods do provide accurate analysis values, they do not permit real time detection and control. Physical processes employing spectrally broadbanded light sources have also been employed which, however, do not permit selective measurements due to transverse sensitivity to water lines. Or, ultimately, laser spectroscopy has been utilized which operates with lead salt diode lasers. The latter, due to the necessity of low operating temperatures (15°–150° K.), require expensive helium cooling elements.

The last mentioned lead salt diode laser spectrometers are expensive since they require expensive He cooling elements. Moreover, the lead salt diode laser is a multimode laser, and thus involves additional expenditures (monochromator) to provide for wavelength selection in the beam path. The same applies for devices with In, Ga, or As/GaAs operating in the room temperature range. They also require a monochromator for wavelength selection, are all equipped with exclusively prismatic beam dividers to split the beam into a reference beam and a measuring beam, and use a multichannel boxcar integrator system for signal processing.

SUMMARY OF THE INVENTION

It is an object of the present invention to improve the above-mentioned process in such a way that a highly selective process gas measuring device which is stable over a long period of time is able to perform continuous, fully automatic process monitoring under industrial conditions.

The above object is achieved according to the present invention by a method of continuously measuring the concentration of at least one component of a gas sample by means of a laser including charging the gas sample with radiation from a laser at a frequency in the range of an absorption line of the component to be measured, detecting a measurement signal corresponding to the intensity of the transmitted radiation, and evaluating the detected measurement signal to determine the extinction, and thus the concentration of the gas component; wherein a single mode laser is employed as the laser providing the radiation; the laser is linearly tuned by means of bandwidth, i.e., line width modulation about a gas specific absorption line so that at least two different intensity measurement values are obtained for the transmitted radiation; and the two different intensity measurement values are utilized in the step of evaluating.

According to one embodiment of the apparatus according to the invention, the tuning is achieved by varying the frequency or wavelength of the laser resonator in that a portion of the laser light is fed back into the laser resonator, and the quantity of light fed back into the laser resonator is cyclically changed, while maintaining the laser current and temperature constant.

According to a further embodiment of the apparatus according to the invention, linear tuning is achieved by varying the frequency or wavelength of the laser resonator in that the current to the laser is periodically changed while maintaining a constant laser temperature.

According to a preferred feature of the invention, the method includes the following steps prior to evaluation of the detected signals: dynamically detecting the direct component of a reference intensity, which occurs as a signal offset, in the measured signal; and making said reference intensity in the measured signal equal to zero (reduction to zero) by the addition of a corresponding countervoltage ($-U_o$) to the measured signal, whereby the detection sensitivity is increased.

Thus, the present invention provides for the use of specific single-mode laser diodes having fixed spectral characteristics at fixed operating parameters for current and temperature. By reducing the number of optical components to a minimum, the system is simultaneously thermally stabilized and prevents thermally caused signal drifts. A newly developed electronic evaluation system reduces the signal component $I_o$ (reference intensity), which component is not relevant to the absorption, to zero and splits the signal pulse into three time windows, $I_o'$ (reference signal to prior to HF absorption signal), $I_{abs}$ (absorption signal) and $I_o^2$ (reference signal following the HF absorption signal). By using $I_o^2$ and subsequent signal integration and averaging in adjustable time steps, the use of a boxcar integrator is made superfluous. The conversion (logarithming) to extinction and concentration, respectively, is performed by a coupled-on personal computer in a conventional manner. The optical system may be constructed of fiberoptic components known from the communications art.

The invention will be described in greater detail below with reference to two embodiments.

DETAILED DESCRIPTION OF THE PREFERRED EMBODIMENTS

Figure 1:
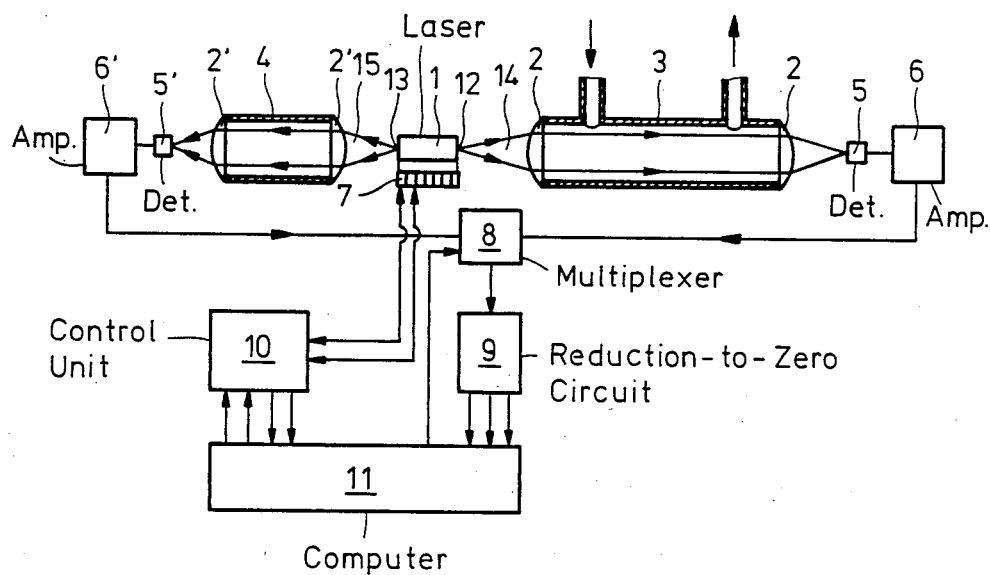
FIG. 1 is a schematic block diagram of one embodiment of an apparatus according to the invention for carrying out the method according to the invention.
Figure 2:
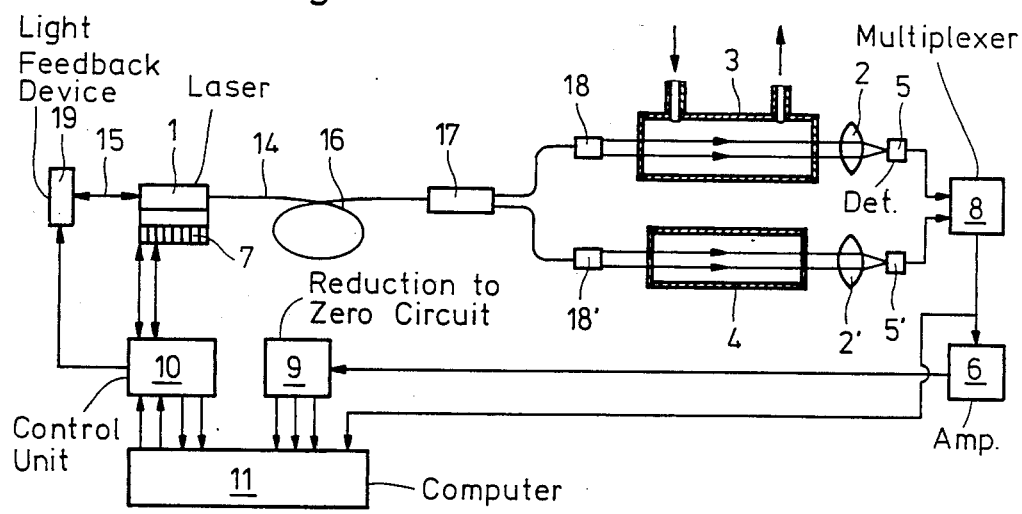
FIG. 2 is a schematic block diagram of another embodiment of an apparatus according to the invention for carrying out the method according to the invention.

The systems shown in FIGS. 1 and 2, which serve to implement the method according to the invention, primarily include a single mode diode laser 1 which is tuned periodically with respect to its wavelength about an absorption line of the gas to be measured, in the present case HF (hydrogen fluoride). The advantage of such a laser 1 lies in the emission of one longitudinal resonator mode. The spectral halfwidth lies in a range from 1/10 to 3 nm, depending on the structure. DFB lasers (Distributed Feedback Laser) have the advantage of a single beam emission characteristic in the near field. The Gaussian distributed intensity characteristic of such laser diodes 1 is realized by selective excitation of the transverse fundamental mode $TEM_{00}$. Single mode intensity distribution in the near and far fields reduces useful signal superpositions by multiple beam interferences in the optical beam path, as they occur when higher order transverse modes are excited with lasers having complicated emission characteristics.

According to the embodiment of FIG. 1, partial laser beams 14 and 15 exiting from the two equal priority outputs 12 and 13, respectively, of laser 1 irradiate, via respective field lenses 2 and 2' the measuring cuvette 3 and the reference cuvette 4, respectively, with the transmitted radiation being directed toward respective detectors 5 and 5'. The detected measurement and reference signals from the respective detectors 5 and 5' travel through respective preamplifiers 6 and 6' to a computer controlled multiplexer 8 and from there to a system computer 11 via an intermediately connected reduction-to-zero circuit 9 having three analog outputs for two signal reference channels ($I_o'$ and $I_o^2$) and a measuring channel. In a conventional manner, this system computer 11 includes an AD/DA converter unit for signal evaluation and is equipped with a data output, an instrument control device and an error diagnostics unit.

In this embodiment without a beam divider, the laser waves from laser 1 are tuned by periodically changing the laser current and keeping the laser temperature constant (see Federal Republic of Germany DE-OS No. 2,362,935, published July 4, 1974, corresponding to U.S. application Ser. No. 320,401 filed Jan. 2, 1973, now U.S. Pat. No. 3,805,074). By changing the injected charge carrier density, the occupation density changes in the conduction band, resulting in a change in the frequency of the induced radiative transition due to displacement of the Fermi edge. In addition, the laser resonator is detuned by Ohmic heating in the transition zone, which changes the inherent frequencies and thus tunes the laser about the absorption wavelength of the gas to be measured. A control unit 10, which performs a two-stage laser thermostat setting by way of an external and an internal Peltier element 7 in the laser module and which further includes an AD/DC laser current driver and devices for measuring temperature and current, is provided for this purpose.

According to the embodiment of FIG. 2 (wherein the same references numerals are used for corresponding parts), the output beam 14 of laser 1 is directed by way of a monomode fiber 16 to a Y-shaped fiber coupler 17 which serves as a beam divider, and is transmitted from there in divided form by way of respective miniature lenses 18 and 18' through the measuring cuvette 3 and the reference cuvette 4 and associated field lenses 2 and 2', respectively. The transmitted beam components detected by respective detectors 5 and 5' are fed via multiplexer 8 to preamplifier 6 and/or system computer 11, respectively. The output of the amplifier 6 is fed via the reduction-to-zero circuit 9 to the computer 11 analogously to the embodiment of FIG. 1. In this embodiment, laser 1 is controlled by means of laser control unit 10 by means of the basic thermostat setting via Peltier element 7 so as to maintain the laser temperature constant and by means of a light feedback element 19 for output radiation 15 from the second output of laser 1 (a feedback-induced line broadening in cw channel-substrate planar laser diodes is principally described in R. O. Miles et al, Appl. Phys. Lett., Vol. 37, No. 11, Dec. 1, 1980, FIG. 1).

The detection systems of both embodiments serve to detect the radiation intensity, which has been specifically weakened by the gas to be measured, in measuring and reference gas cuvettes 3, 4. The resulting absorption signal is conducted through preamplifiers 6 and multiplexer 8 to evaluation unit or computer 11. Evaluation unit 11 serves to detect the signal intensity in the measurement channel and in the reference channel. Before integration over time and sliding average formation with adjustable time interval (RC network), according to a feature of the invention the signal components not relevant to absorption are separated by the electronic reduction-to-zero system 9. Reference cuvette 4 is hermetically sealed and has a known static HF concentration.

The concentration proportional absorption signal is detected on the measuring path and, by way of a desired value/actual value comparison, serves to periodically calibrate the concentration of the system. The control paths 10, 7 of FIG. 1, or 10, 7, and 19 of FIG. 2, which in turn are controlled by system computer 11, serve to regulate the tuning of the laser about the gas specific absorption line $\nu_o$ of FIG. 3.

In a conventional manner, computer 11 also serves to monitor and control the operating parameters of the laser 1, the parameters of the measuring gas and to calculate and provide an output of the concentration of the measuring gas.

In the embodiment according to FIG. 2, the wavelength of laser output 14 is tuned by a change in the amount of light fed back into the laser resonator via the feedback device 19.

Figure 3:
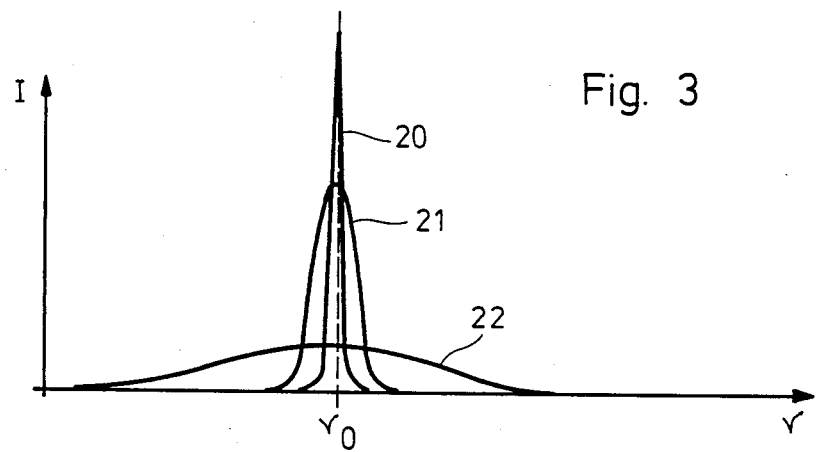
FIG. 3 shows frequency curves used to explain the present invention.

In contrast to tuning by current pulses, in which the wavelength of the spectral centroid of a laser mode is tuned at a constant halfwidth by a variation in time of the laser current and/or the laser temperature, tuning by way of optical feedback device 19 cyclically varies the frequency bandwidth (halfwidth) of the laser mode (see FIG. 3).

Since the laser current and the laser temperature ar kept constant, the wavelength of the spectral centroid then remains constantly tuned about the average absorption wavelength 20 ($\nu_o$) of the gas (HF) to be measured.

Light feedback device 19 (see R. O. Miles et al; part of FIG. 1) couples only a few percent of the light intensity 15 emitted at the second output 13 of laser 1 back into the laser resonator. The amount of feedback is varied periodically to realize a change over time in the spectral bandwidth of the laser mode between states 21 and 22 (FIG. 3). The wavelength of the spectral centroid 20 or, more precisely, frequency $\nu_o$, coincides with the wavelength of the spectral centroid of the gas to be measured. The periodic change in bandwidth of the laser mode causes the absorption intensity at detectors 5 and 5' to be modulated.

The following equation applies for the change in intensity $I(+)$ over time:

$$I(+) \sim \frac{1}{\delta_{laser}^{(+)} + \delta_{gas\,line}} \sim \frac{1}{\delta_{laser}^{(+)}} \quad (1)$$

where $\gamma$ represents the half-width values of the laser emission and molecule absorption lines.

If the laser line is broadened 40 times (with a feedback of 0.1%), the absorption intensity drops to about 2.5% of the original value with an infinitely narrow spectral bandwidth of the laser ($\gamma(t)$−laser=0). In the case of $\gamma(t)=\gamma$ gas line the value lies at 50% of the original change in intensity due to gas absorption.

Since the laser line is more narrowbanded by a factor of 10-100 than the gas absorption line to be measured, the following equation applies, in good approximation, for the maximum change in power $\Delta P$ caused by absorption:

$$\Delta P \sim \frac{1}{\delta_{gas\,line}} \quad (2)$$

Figure 4:
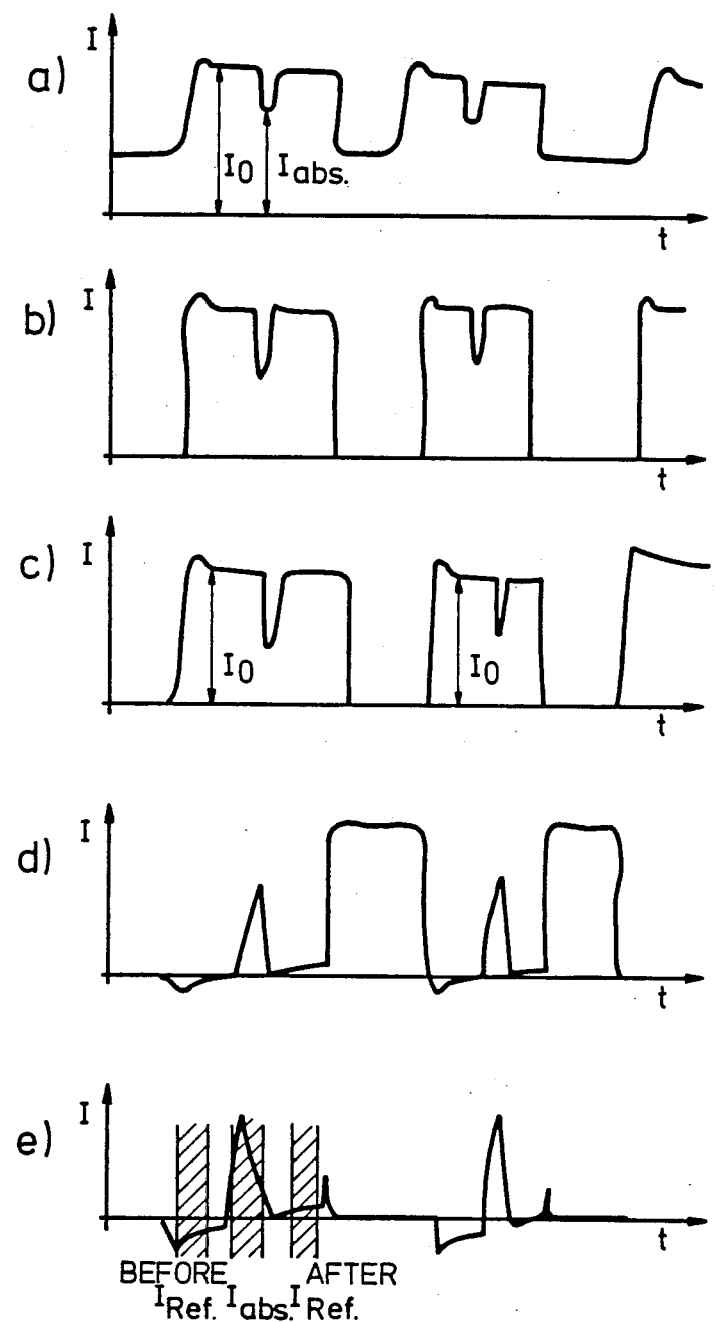
FIGS. 4a–4e show the measured signal over time during various signal shaping stages in the reduction-to-zero Stage 9 of FIGS. 1 and 2.

To increase detection sensitivity by improving the signal dynamics for small changes in the absorption signal, the direct current component of the reference intensity $I_o$ occurring as a signal offset is dynamically compiled and, by adding a countervoltage ($-U_o$) corresponding to $I_o$ is made to equal zero, i.e., $I_o'=0$ (reduction to zero). The time diagram for the pulse shaping procedure is shown in Figures 4a to 4e. The respective processing steps shown in these figures take place in the stages of the electronic reduction-to-zero system 9. FIG. 4a shows the intensities $I_o$ and $I_{abs}$ over time. According to FIG. 4b, the pause pulse has been subtracted. FIG. 4c shows the dynamic peak value measurements of $I_o$ for every measurement pulse. In FIG. 4d, a negative countervoltage $-U_o$ corresponding to $-I_o$ is added to the signal and additionally the signal is inverted. FIG. 4e shows the signal regions $I_{Ref}^{before}$, $I_{abs}$ and $I_{Ref}^{after}$, divided after separation of the pause pulses.

In the evaluation unit or computer 11, conventional evaluation processes can be used to measure the change in power $\Delta P$ occurring as a result of the specific gas absorption and the extinction value is determined according to the following equation:

$$E=\ln(I_o/I_{abs}) \quad (3)$$

Figure 5:
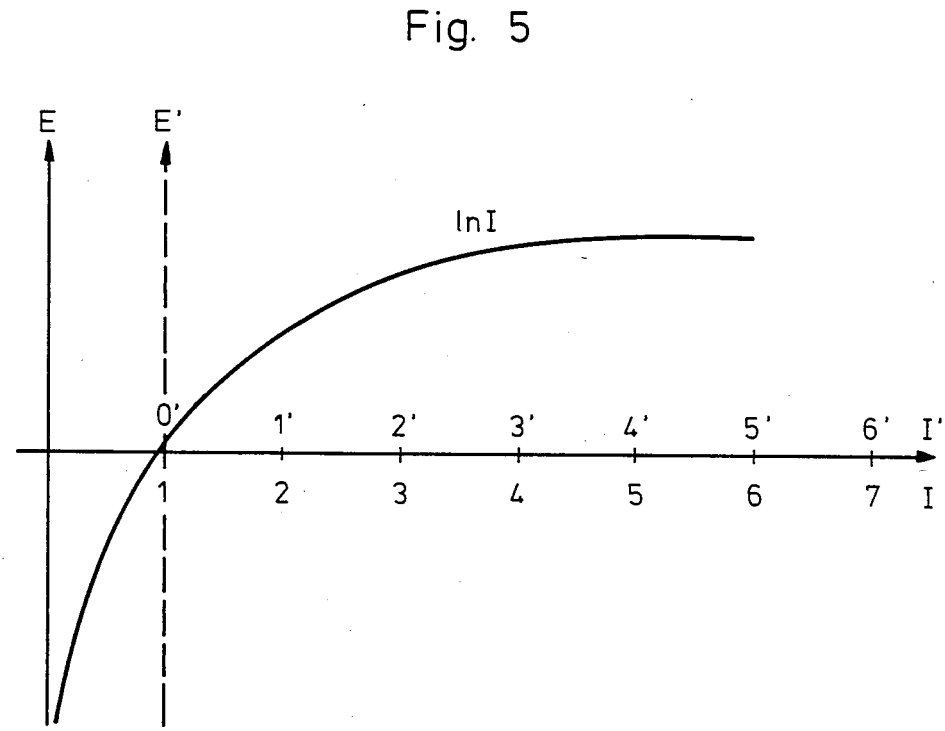
FIG. 5 is a curve showing the relationship between extinction calculated in the conventional manner and the extinction calculated after transformation of the intensity values according to the invention.

However, for a weak specific gas absorption, $I_o/I_{abs}$ differs only slightly from 1, with the absolute signal values $I_o$ and $I_{abs}$ possibly taking on very high values. To improve the dynamic of the subsequently conncted evaluation system 11, particularly the logarithming member, when evaluating such a weak specific gas absorption, the signal intensities are transformed in such a manner that the standard for $I_o$ always remains at the zero level as shown in FIG. 5. This transformation is realized by the so-called "reduction to zero" of signal $I_o$ in the circuit 9.

Reduction to zero corresponds to a transformation of intensities $I$ to $I'$, where the following applies:

$$\begin{aligned} I' &= I - 1 \quad \text{with} \quad I_o' = 0 \text{ and} \\ E' &= E \quad \quad\quad \ln I_o = 0 \end{aligned} \quad (4)$$

If the extinction E in the "old" coordinate system is expressed by the deleted intensity values, the following results according to Equation (3) and (4):

$$E = \ln \frac{I_o}{I_{abs}} \qquad E = \ln \frac{I_o + 1}{I_{abs} + 1}$$

With $I_o'=0$ (reduction to zero) the following applies:

$$E = \frac{1}{I_{abs}' + 1} = \ln 1 - \ln(I_{abs}' + 1)$$

and from this results the following equation:

$$E = |-\ln(I_{abs}'+1)| \quad (5)$$

as an expression of the extinction upon measurement of the intensities reduced to zero. By eliminating the signal component $I_o$ which appears as an offset in the logarithming stages, there thus results an improvement in signal resolution by a factor of 100 compared to the conventional method.

It will be understood that the above description of the present invention is susceptible to various modifications, changes and adaptations, and the same are intended to be comprehended with the meaning and range of equivalents of the appended claims.

What is claimed is:

1. In a method of continuously measuring the concentration of at least one component of a gas sample by means of a laser including charging the gas sample with radiation from a laser at a frequency in the range of an absorption line of the component to be measured, detecting a measurement signal corresponding to the intensity of the transmitted radiation, and evaluating the detected measurement signal to determine the extinction, and thus the concentration of the gas component, the improvement comprising: employing a single mode laser as the laser providing the radiation; linearly tuning the laser by means of bandwidth modulation about a gas specific absorption line so that at least two different intensity measurement values are obtained for the transmitted radiation; and utilizing said two different intensity measurement values in said step of evaluating.

2. A method as defined in claim 1, wherein said step of linearly tuning includes: feeding a portion of the laser light back into the laser resonator; and cyclically changing the quantity of light fed back into the laser resonator, while maintaining the laser current and temperature constant.

3. A method as defined in claim 2, further comprising: the following steps prior to said step of evaluating: dynamically detecting the direct component of a reference intensity, which occurs as a signal offset, in each measured signal; and making said reference intensity equal to zero (reductin to zero) by the addition of a corresponding countervoltage ($-U_o$) to each measured signal, so that the detection sensitivity is increased.

4. In a method of continuously measuring the concentration of at least one component of a gas sample by means of a laser including charging the gas sample with radiation from a laser at a frequency in the range of an absorption line of the component to be measured, detecting a measurement signal corresponding to the intensity of the transmitted radiation, and evaluating the detected measurement signal to determine the extinction, and thus the concentration of the gas component, the improvement comprising: employing a single mode laser as the laser providing the radiation; linearly tuning the laser about a gas specific absorption line so that at least two different intensity measurement values are obtained for the transmitted radiation; utilizing said two different intensity measurement values in said step of evaluating; and increasing the detection sensitivity by, prior to said step of evaluating, dynamically detecting the direct component of a reference intensity, which occurs as a signal offset, in each measured signal, and making said reference intensity equal to zero by the addition of a corresponding countervoltage ($-U_o$) to each measured signal.

5. A method as defined in claim 4 wherein said step of linearly tuning comprises varying the frequency or wavelength of the laser resonator.

6. A method as defined in claim 5, wherein said step of varying the frequency or wavelength includes periodically changing the current to the laser while maintaining a constant laser temperature.

7. In an apparatus for continuously measuring the concentration of at least one component of a gas sample including a reference cuvette containing a reference sample of the gas to be measured, a measuring cuvette through which the gas to be measured is flowing, a laser for producing radiation at a frequency in the range of an absorption line of the gas component to be measured, means for directing the radiation from said laser through each of said measuring and reference cuvettes, first and second detector means for detecting the radiation after passing through the respective said measuring and reference cuvettes, and means responsive to at least the output signals from said first and second detector means for controlling said laser and for evaluating the detected signal produced by said first detector means to determine the extinction, and thus the concentration of the gas component; the improvement wherein: said laser is a single mode laser having first and second primary outputs; and means are provided for linearly tuning said laser by means of bandwidth modulation about a gas specific absorption line so that at least two different intensity measurement values are obtained for the radiation transmitted through said measuring cuvette.

8. Apparatus as defined in claim 7 wherein: said means for directing the radiation includes means for dividing the laser beam at said first output into two divided beams which are directed respectively through said measuring cuvette and said reference cuvette; the output signals from said first and second detector means are fed to said means for evaluating via a multiplexer and a series connected preamplifier; and said means for linearly tuning includes means for feeding a cyclically varying portion of the radiation at said second output back to the resonator of said laser, while maintaining the laser current and temperature constant.

9. Apparatus as defined in claim 8, further comprising means for increasing the detection sensitivity connected between said preamplifier and said means for evaluating, with said means for increasing the detection sensitivity including means for dynamically detecting the direct component of a reference intensity, which occurs as a signal offset, in each measured signal, and for making said reference intensity equal to zero (reduction to zero) by the addition of a corresponding countervoltage ($-U_o$) to each measured signal.

10. In an apparatus for continuously measuring the concentration of at least one component of a gas sample including a reference cuvette containing a reference sample of the gas to be measured, a measuring cuvette through which the gas to be measured is flowing, a laser for producing radiation at a frequency in the range of an absorption line of the gas component to be measured, means for directing the radiation from said laser through each of said measuring and reference cuvettes, first and second detector means for detecting the radiation after passing through the respective said measuring and reference cuvettes, and means responsive to at least the output signals from said first and second detector means for controlling said laser and for evaluating the detected signal produced by said first detector means to determine the extinction, and thus the concentration of the gas component; the improvement wherein: said laser is a single mode laser having first and second primary outputs; said means for directing the radiation includes a first lense for directing the output radiation at said first output through said measuring cuvette and a second lense for directing the radiation at said second output through said reference cuvette; the output signals from said first and second detector means are fed to said means for evaluating via respective series connected preamplifiers and a multiplxer; and means are provided for linearly tuning said laser about a gas specific absorption line so that at least two different intensity measurement values are obtained for the radiation transmitted through said measuring cuvette, with said means for linearly tuning including means for periodically changing the laser current while maintaining the laser temperature constant.

11. Apparatus as defined in claim 10, further comprising means for increasing the detection sensitivity connected between said multiplexer and said means for evaluating, with said means for increasing the detection sensitivity including means for dynamically detecting the direct component of a reference intensity, which occurs as a signal offset, in each measured signal, and for making said reference intensity equal to zero (reduction to zero) by the addition of a corresponding countervoltage ($-U_o$) to each measured signal.

* * * * *